United States Patent [19]

Müllner et al.

[11] Patent Number: 5,780,592
[45] Date of Patent: Jul. 14, 1998

[54] COMPOSITIONS COMPRISING LIPOPROTEINS AND CROTONAMIDE DERIVATIVES

[75] Inventors: Stefan Müllner, Hochheim; Axel Hofmann, Frankfurt; Karin Saar, Biebesheim; Hans-Ulrich Schorlemmer, Marburg; Robert Bartlett, Darmstadt, all of Germany

[73] Assignee: Hoechst Aktiengesellschaft, Frankfurt am Main, Germany

[21] Appl. No.: 761,335

[22] Filed: Dec. 10, 1996

[30] Foreign Application Priority Data

Dec. 20, 1995 [DE] Germany ............ 195 47 648.4

[51] Int. Cl.$^6$ ............ C07K 1/00; A61K 31/42; A61K 31/275
[52] U.S. Cl. ............ 530/359; 514/2; 514/378; 514/464; 514/465; 514/521; 514/522; 424/283.1; 549/439; 558/392
[58] Field of Search ............ 530/359; 514/2, 514/464, 465, 378, 521, 522; 424/283.1; 558/392; 549/439

[56] References Cited

U.S. PATENT DOCUMENTS

| | | | |
|---|---|---|---|
| 4,061,767 | 12/1977 | Ertel et al. | 424/282 |
| 5,240,960 | 8/1993 | Hambleton et al. | 514/521 |
| 5,308,865 | 5/1994 | Bartlett et al. | 514/465 |
| 5,384,423 | 1/1995 | Hambleton et al. | 558/392 |

FOREIGN PATENT DOCUMENTS

| | | |
|---|---|---|
| 0529500 | 3/1993 | European Pat. Off. |
| 0538783 | 4/1993 | European Pat. Off. |

OTHER PUBLICATIONS

Ananth et al., "Apolipoproteins A–I and B and Cholesterol in Synovial Fluid of Patients With Rheumatoid Arthritis", Metabolism, 42(7):803–806 (Jul. 1993).

Schorlemmer et al., "Therapeutic activity of leflunomide in acute and chronic relapsing experimental allergic encephalomyelitis", Agents Action 41, Special Conference Issue: C271–C273 (1994).

Garton et al., "Pseudosepsis in Rheumatoid Arthritis due to Cellular and Lipid Abnormalities in Synovial Fluid", British J. of Rheumatology, 31:625–626 (1992).

Q. Xu et al., "Lipid utilization by human lymphocytes is correlated with high–density–lipoprotein binding site activity", Biochem. J., 285:105–112 (1992).

Biochemie der Lipoproteine, pp. 15–31 and 44–53 (In German) (date is not available).

Primary Examiner—Cecilia J. Tsang
Assistant Examiner—Abdel A. Mohamed
Attorney, Agent, or Firm—Finnegan, Henderson, Farabow, Garrett & Dunner, L.L.P.

[57] ABSTRACT

A composition comprising lipoproteins and a compound of the formula I

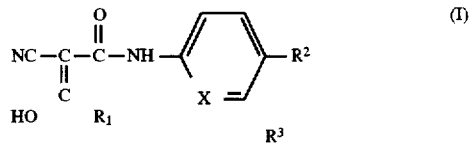

stereoisomeric form or salt thereof, suitable for the treatment of immunological disorders, cancer or in transplantation.

21 Claims, No Drawings

COMPOSITIONS COMPRISING LIPOPROTEINS AND CROTONAMIDE DERIVATIVES

DESCRIPTION

The term lipoprotein refers to high-molecular weight, water-soluble complexes consisting of lipids (cholesterol, triglycerides, phospholipids) and one or more very specific proteins which can complex lipids and are described as apolipoproteins. The lipoproteins are the functional units for the transport of water-insoluble lipids in the blood. It is common to the structure of lipoproteins that the hydrophilic portions of the phospholipids and the hydrophilic portions of the apolipoproteins are arranged on the surface and the hydrophobic triglycerides and cholesterol esters, on the other hand, are arranged in the interior of the spherical particle (pseudomicellar particle).

The lipoproteins are divided into various density classes. Lipids have a significantly lower density than proteins. For the former, the specific weight is under 0.9 g/ml of KBr, whereas for the proteins it is over 1.28 g/ml of Kbr. Complexes of lipids and proteins accordingly have densities between the extreme values mentioned. In the ultracentrifuge, the lipoproteins can be separated into 4 density classes.

Chylomicrons (density d<0.95 g/ml) are formed in the intestine and transport exogenic triglycerides, their lipid content is 98–99.5%, the protein content 0.5–2%; they form a cream in the serum.

VLDL (=very low density lipoproteins; d<1.006 g/ml ) are formed in the liver and transport the main proportion of the endogenous triglycerides and consist to 85–90% of lipids and to 10–15% of protein. IDL (intermediate density lipoproteins; d=1.006–1.019 g/ml) are only detectable in very low concentrations in metabolically healthy people and are seen as metabollic products of VLDL or precursor molecules of LDL.

LDL (low density lipoproteins; d=1.019–1.063 g/ml) transport the main proportion of the cholesterol in the blood. LDLs are formed as a metabolic product from VLDLs and contain approximately 75% lipids and 25% proteins.

HDL (=high density lipoproteins; d=1.063–1.21 g/ml) contain approximately 50% protein and 50% lipids and are formed as precursor molecules by the intestine and liver and shaped in the plasma; they can absorb cholesterol from the cells and transport it back to the liver. On the basis of the different composition and morphology and also functional properties, the HDL subfractions $HDL_1$ (1.055–1.085 g/ml), $HDL_2$ (1.063–1.12 g/ml) and $HDL_3$ (1.12–1.21 g/ml) are differentiated.

HDLs are not a homogeneous substance, but rather a heterogeneous mixture of macromolecules which differ in particle size, chemical composition and physicochemical properties. A reference method for the preparation of the HDLs is flotation in the preparative ultracentrifuge (d=1.063–1.21 g/ml). The major part of the particles found in this density class have the following properties:

a) electrophoresis: migration in the α-position, b) electron microscopy, spherical particles having a diameter of $80-120 \times 10^{-10}$ m, c) chemical composition: Apo A-I content (30–35%), Apo A-II content (10–15%), Apo C content (3–5%), phospholipid content (25–30%), cholesterol/cholesterol ester content (15–20%), triglyceride content (3–5%).

Depending on the isolation technique and the content of lipoproteins (a) in various sera, variable amounts of Apo-B-containing lipoproteins (lipoprotein (a), LDL) may be found in the HDL density class; on the other hand, small losses of HDL in the d>1.21 g/ml density class are recorded on preparative ultracentrifugation.

The HDL fraction can be separated into various subfractions by special isolation techniques. The subfractions most important for clinical interests are designated as $HDL_1$ (1.055–1.085 g/ml), $HDL_2$ (1.063–1.125 g/ml) and $HDL_3$ (1.125–1.210 g/ml). They are distinguished by different lipid and protein compositions, physicochemical and functional properties.

The subfraction $HDL_1$ can be isolated by special separation techniques (e.g. zonal centrifugation, heparin affinity chromatography). It contains Apo E as the dominant protein component. With cholesterol feeding, the concentration of this fraction greatly increases in various animal species; this cholesterol-reduced HDL fraction is designated as $HDL_C$. $HDL_C$ is also detectable in humans after several weeks of cholesterol-rich food.

Approximately 50% of the HDL material is protein, 30% is phospholipids, 10 to 20% cholesterol and cholesterol esters and 5% triglycerides. The lecithin/sphingomyelin ratio is 5:1, and the ratio of esterified cholesterol/free cholesterol is approximately 3:1. $HDL_2$ contains approximately 60% lipids and 40% protein, while $HDL_3$ consists to approximately 45% of lipids and to approximately 55% of proteins. The phosphatidylcholine/sphingomyelin ratio of free to esterified cholesterol is higher in $HDL_2$ than in $HDL_3$. $HDL_C$ contains a particularly high content of Apo E and cholesterol esters. The protein content of the HDL is made up of several apolipoproteins. Approximately 90% of the protein content of the HDL consists of Apo A-I and Apo A-II. The quantitative ratio of both apolipoproteins appears to be different in the subpopulations of the HDL and in some cases a molar Apo A-I/Apo A-II quotient of 9:1 in the $HDL_2$ fraction and a quotient of 2:1 in the $HDL_3$ fraction of the respective preparation were found using the zonal rotor.

Crotonamide derivatives, their preparation and their use as pharmaceuticals are disclosed in EP 484 223, EP 529 500, EP 538 783, U.S. Pat. No. 4,061,767 and EP 551 230.

It has now been found that compounds of the formula I concentrate in the HDL fraction of the blood. The present invention is directed to a composition comprising a claimed crotonamide derivative and lipoprotein. Preferred compositions comprise one or more lipoprotein derived from animal source, and especially preferred are lipoproteins derived from mammalian, and in particular, human, source. Suitable lipoproteins may be naturally occurring or modified lipoproteins. Preferred compositions comprise one or more high density lipoprotein and a compound of the formula I.

Compositions of the present invention lead to a dose reduction of the compound of the formula I with the same activity. The dose reduction leads, without decreased activity, to increased safety on therapeutic use. At the same time, the costs of therapy can be reduced. Furthermore, preparations containing high density lipoproteins and compounds of the formula I show prolonged activity in transplantations.

The invention therefore relates to a preparation comprising 1) a lipoprotein, and 2) a compound of the formula I

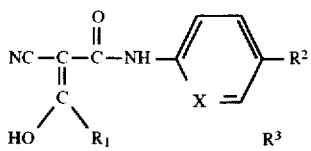

or a stereoisomeric form of the compound of the formula I, or a salt of the compound of the formula I, where $R^1$ is
- a) $(C_1-C_4)$-alkyl
- b) $(C_3-C_5)$-cycloalkyl,
- c) $(C_2-C_6)$-alkenyl or
- d) $(C_2-C_6)$-alkynyl, $R^2$ is
- a) —$CF_3$,
- b) —O—$CF_3$,
- c) —S—$CF_3$,
- d) —OH,
- e) —$NO_2$,
- f) halogen,
- g) benzyl,
- h) phenyl,
- i) —O-phenyl,
- k) —CN
- l) —O-phenyl, mono- or polysubstituted by
  1) $(C_1-C_4)$-alkyl,
  2) halogen,
  3) —O—$CF_3$ or
  4) —O—$CH_3$, $R^3$ is
- a) $(C_1-C_4)$-alkyl,
- b) halogen, or
- c) a hydrogen atom, and X is
- a) a —CH group or
- b) a nitrogen atom.

The use of a compound of the formula I, a stereoisomeric form of the compound of the formula I, or a salt of the compound of the formula I is preferred, where $R^1$ is
- a) methyl,
- b) cyclopropyl or
- c) $(C_3-C_6)$-alkynyl, $R^2$ is $CF_3$ or CN, $R^3$ is a hydrogen atom or methyl, and X is a —CH group.

The use of N-(4-trifluoromethylphenyl)-2-cyano-3-hydroxycrotonamide, 2-cyano-3-cyclopropyl-3-hydroxy-N-(4-cyanophenyl)acrylamide or N-(4-trifluoromethyl phenyl)-2-cyano-3-hydroxyhept-2-en-6-yne-carboxamide, stereoisomeric forms thereof, or their corresponding salts, is particularly preferred.

The compounds of the formula I are prepared by known processes, such as are described in EP 484 223; EP 538 783 or EP 551 230.

The term alkyl, alkenyl or alkynyl is understood as meaning radicals whose carbon chain can be straight-chain or branched. The term "$(C_1-C_4)$"-alkyl" means a carbon chain, straight or branched, containing one to four carbon atoms. The alkenyl or alkynyl radicals can furthermore contain two or more double bonds or two or more triple bonds. The term "$(C_2-C_6)$-alkenyl" means a carbon chain containing two to six carbon atoms with one or more double bonds. The term "$(C_2-C_6)$-alkynyl" means a carbon chain, straight or branched, containing two to six carbon atoms wherein one or more triple bonds. Cyclic alkyl radicals are, for example, 3- to 5-membered monocyclic systems such as cyclopropyl, cyclobutyl or cyclopentyl. The term "$(C_3-C_5)$ cycloalkyl" means a cyclic carbon chain containing three to five carbon atoms. The starting substances for the chemical reactions are known or can easily be prepared by methods known from the literature.

The term "halogen" means F, Br, I or Cl ion.

The term "O-phenyl, mono- or polysubstituted by" means an O-phenyl comprising one to five substituents independently selected from the indicated group.

Salt forms of a compound of formula I may be formed by means known to those in the art. Typically, acid addition salt forms are preferred. Acid addition salts mean any non-toxic organic or inorganic acid addition salt of the base compounds represented by formula I. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as benzenesulfonic acid, methanesulfonic acid, and 2-hydroxyethanesulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

One or more excipients may be added to the composition. Acceptable excipients are well known to those in the art. Excipients may be added to facilitate large scale handling of the composition, or may be added to enhance pharmaceutical parameters such as stability or solubility. Particularly preferred are pharmaceutically acceptable excipients, which include glidants, antifoaming agents, preservatives, antioxidants, buffering agents, chelating agents, coating agents, colors or dyes, complexing agents, desicants, emulsifying and/or solubilizing agents, filtering agents, humectants, plasticizers, solvents, sorbents, stiffening agents, suppository bases, suspending and/or viscosity-increasing agents, sweetening agents, tablet binders, tablet and/or capsule diluents and/or lubricants, disintegrants, tonicity agensts, vehicles and wetting and/or solubilizing agents.

Lipoprotein as used in the present invention may be naturally occurring, such as derived from animal source, or non-naturally occurring and includes chemically modified lipoproteins. Especially preferred are lipoproteins derived from a mammalian, and in particular, human, source. Suitable lipoproteins may be obtained from mammals such as cattle, horses or rabbits. Lipoprotein from the patient to be treated is particularly suitable, as autologous lipoprotein has less, if any, toxicity and immunogenecity than lipoprotein from mammals.

Lipoprotein is composed of a lipid and protein. Preferred lipids are those naturally occurring in blood or serum, such as cholesterol, cholesterol esters, phospholipids and triglycerides. Preferred proteins are lipophilic proteins, particularly preferred are lipophilic proteins isolated from blood or serum. Proteins may be chemically modified proteins, such as polyethyleneglycol modified proteins. The preferred protein to lipid ratio is about 20% protein to about 80% lipid, a more preferred ratio is about 30% protein to about 70% lipid, and even more preferred ratio is about 40% protein to about 60% lipid. The most preferred ratio of protein to lipid is about 45% protein to about 55% lipid to about 50% protein to about 50% lipid. Preferred ratios of lipid components vary with regard to the lipoprotein used. However, the lipid components may comprise about 5% to about 40% phospholipids. The lipid component may comprise about 1% to about 20% triglycerides. The lipid component may comprise about 5% to about 30% cholesterol esters. The lipid component may comprise about 1% to about 5% cholesterol.

Compositions of the present invention comprise about 1% to about 20%, by dry weight of the dry composition, of a compound of formula I or a salt thereof.

Particularly preferred are HDL lipoproteins, especially autologous HDL. However, HDL fractions, subfractions or HDL constituents can also be employed in the preparation according to the invention. In addition, HDL may be modified chemically or enzymatically.

The preparation according to the invention is suitable, for example, for the treatment of immunological disorders carcinomatous disorders such as lung cancer, leukemia, ovarian cancer, sarcoma, Kaposi's sarcoma, meningioma, colonic cancer, lymph node cancer, brain tumors, breast cancer, pancreatic cancer, prostatic cancer or skin cancer autoimmune disorders such as systemic lupus erythematosus or multiple sclerosis rheumatic disorders transplantations or graft-versus-host reactions or host-versus-graft reactions acute, chronic or hyperacute rejection reactions after transplantation of organs such as kidney, heart, skin, liver, bone, blood or hair disorders which are caused by highly proliferating cells psoriasis or atypic dermatitis allergy, asthma, urticaria, rhinitis or uveitis type II diabetes cystic fibrosis, colitis, fibrosis of the liver or sepsis.

The invention also relates to a process for the production of the composition, which comprises admixing a compound of the formula I, a stereoisomeric form thereof or a salt of the compound of the formula I, and a lipoprotein. Particularly preferred is a process for the production of the composition wherein the composition is in a suitable administration form using a pharmaceutically acceptable excipient and, if appropriate, other suitable active compounds, additives or auxiliaries.

The composition according to the invention can be administered intravenously or parenterally. Suitable liquid pharmaceutical administration forms are, for example, injectable solutions, suspensions or emulsions.

Preferably, the composition is prepared and administered in dose units, each unit containing as active constituent a certain dose of the compound of the formula I and/or physiologically tolerable salts of the compound of the formula I. For the treatment of a patient (70 kg), in the early phases an intravenous infusion treatment of about 100 mg per day to about 1200 mg per day, with at most 1200 mg per day. A more preferred range of doses is about 300 mg per day to about 600 mg per day. In the later rehabilitation phase, a maximum of 3 times 300 mg per day of the compound of the formula I, stereoismeric form thereof or the corresponding salts of the compound of the formula I are indicated.

Preferred compositions are tablet forms. Particularly preferred tablet forms are tablets of about 100 mg to about 500 mg, and especially preferred tablets are of about 150 mg to about 250 mg. The preferred amount of a compound of formula I, stereoisomeric form thereof or a salt thereof in each tablet is from about 10 mg to about 50 mg per dosage form, and especially preferred is about 10 mg to about 20 mg.

The amount of lipoprotein, in particular the amount of HDL, in the preparation is from 0.1 ml to 100 ml per day. The quantitative data ml of HDL relates to the preparation as in Example 1a, the serum and the HDL containing no compound of the formula I. The lipoprotein may be a single lipoprotein or a mixture of lipoproteins.

The dose to be used is, of course, dependent on various factors such as the subject to be treated (i.e. human or animal), age, weight, general state of health, the degree of severity of the symptoms, the disorder to be treated, possible concomitant disorders (if present), the nature of the accompanying treatment with other pharmaceuticals or the frequency of treatment. The doses are in general administered two or more times per day and preferably once to three times per day. The amount of the compound of the formula I used is in this case based on the recommended daily dose of the particular compound of the formula I and the solubility of the compound of the formula I in HDL. In general, the concentration of the compound of the formula I in the preparation is from 10% to 100% of the recommended daily dose, preferably from 20% to 80%, in particular 50%. Suitable therapy with the combinations according to the invention thus consists, for example, in the administration of one, two or three individual doses of the preparation according to the invention consisting of 1) 5 mg to 50 mg, preferably from 10 mg to 20 mg, of N-(4-trifluoromethylphenyl)-2-cyano-3-hydroxycrotonamide and 2) 0.1 ml to 10 ml, preferably 1 ml to 3 ml of HDL, the amount naturally being dependent on the number of individual doses and also the illness to be treated. An individual dose can also consist of two or more dose units administered at the same time. The ratio of the compound of the formula I to the amount of HDL in the dose units depends on the solubility of the compound of the formula I in HDL. As a rule, from 0.01 to 10 ml of HDL, preferably from 0.1 ml to 5 ml of HDL, are employed per mg of the compound of the formula I.

Furthermore, the preparations according to the invention can also be employed together with other suitable active compounds, for example antiuricopathics, platelet aggregation inhibitors, analgesics, steroidal or nonsteroidal antiinflammatories or immunosuppressive compounds such as cyclosporin A, FK 506 or rapamycin.

EXAMPLE 1

N-(4-Trifluoromethylphenyl)-2-cyano-3-hydroxycrotonamide (Compound 1) in Lipoprotein Fractions from Human Serum Three male volunteer subjects each receive 100 mg of N-(4-trifluoromethylphenyl)-2-cyano-3-hydroxycrotonamide in powder form orally on three successive days. Approximately four days after the last medication, 100 ml of blood are taken in each case. Serum is obtained from this blood by centrifugation.

a) Preparation of the lipoprotein fractions

The serum of each subject is brought to a density of 1.020 g/ml by stirring in solid KBr, 0.0199 g of KBr being employed per ml of serum. After centrifugation at 4° C. and 140.000×g for 20 hours, a very low density lipoprotein (VLDL)-containing milky-white lipoprotein layer separates from the serum. After carefully pipetting off this layer, the remaining serum is mixed with 0.0628 g of Kbr/ml, a density of 1.063 g/ml being achieved. After centrifugation at 4° C. and 140.000×g for 20 hours, the brownish low density lipoprotein (LDL) layer is removed from the serum. The remaining serum is mixed with 0.234 g of KBr/ml/a density of 1.21 g/ml being achieved. After centrifugation at 4° C. and 140.000×g for 20 hours, the high density lipoprotein (HDL) layer is removed. The HDL fractions obtained are added to a dialysis tube having an exclusion limit of 6000–8000 kD and dialyzed against a pH 7.4 buffer for 72 hours. The buffer is changed 2 to 3 times every 24 hours. The dialyzed HDL fractions can be used immediately or are stored at –80° C. After dialysis, a protein determination is carried out on the dialyzed HDL fractions. A value of approximately 20 mg of protein per ml of dialyzed HDL fraction results.

b) Extraction of compound 1 from the samples

For this purpose, 500 µl are removed from each lipoprotein fraction and additionally from the starting plasma and slowly added dropwise to 1200 µl of acetonitrile in each case. The samples are treated in an ultrasonic bath for 10 min and centrifuged off at 14.000×g for 10 min. Two phases are formed in the HDL samples, of which the upper phase is further processed. The supernatant is removed from all samples and evaporated overnight in a drying oven at 60° C. On the next day the samples are taken up in 100 µl of methanol in each case and analyzed.

c) Analysis method

The samples are analyzed using high-pressure liquid chromatography (HPLC).

Eluent: 0.1M $H_3PO_4$: acetonitrile 1:1

Column: LiChrospher 100 RP 18, 250×4 mm, 5µ, Merck AG

Flow rate: 1.5 ml/min

Injection: 50 µl per sample

Detection: with diode array detector d) Result

A standard curve is plotted in each case using the compound 1. By comparing the UV spectra with the substance found in the samples it can be seen that exclusively compound 1 is present in the plasma. The total amount of the substance detected in the plasma in the three subjects is as follows: subject 1 (S1) 32.00 µg/ml, S2 9.61 µg/ml and S3 32.27 µg/ml. Apart from in the whole plasma, compound 1 can only be found in the HDL fractions. 1.55 µg/ml of the compound 1 are determined in S1, 2.39 µg/ml in S2 and 1.03 µg/ml 1 in S3.

EXAMPLE 2

Influence of HDL on the Action of Compound 1 in the Acute Experimental Allergic Encephalomyelitis (EAE) Test Model The experiment is carried out as described in H. W. Schorlemmer and R. R. Bartlett (Agents Actions, 41, Special Conference Issue: C271–C273, (1994)) incorporated by reference herein. 10 mg of the compound 1 are dissolved in 1 ml of the dialyzed HDL fraction obtained essentially as described in Example 1 from rat serum. For this purpose, 100 mg of compound 1 are added to 10 ml of dialyzed HDL fraction and the mixture is stirred overnight on a magnetic stirrer at a medium stirring speed and 4° C. It is then suspended 3 times for 30 sec using ultrasound and stirred for a further 4 hours. Finally, the preparation is treated in an ultrasonic bath for 15 min. The preparation is administered intravenously to the rats.

Compound 1 without HDL is administered intravenously to the rats in a concentration of 10 mg/ml of solvent (1% carboxymethylcellulose in water). The concentration data in the table in each case relate to 1 kg live weight of a rat. The control group receives only solvent (1% carboxymethylcellulose in water) administered intravenously. In each case 5 Lewis rats are employed per experiment. Table 1 shows the results. The rats were assessed daily for clinical expression of disease and graded on a scale of 0 to 7; 0, healthy; 1, abnormal gait and tail atony; 2, mild but definite weakness of one or both hind legs or mild ataxia; 4, severe parapraesis and minimal hind leg movement; 5, no hind leg movement and paraplegia; 6, a moribund state with no spontaneous movement and impaired respiration; the last two grades were accompanied by increasing degrees of front leg involvement as well as urinary and fecal incontinence; 7, death.

TABLE 1

| Days after injection | Compound 1 20 mg/kg rat | Compound 1 10 mg/kg rat | Compound 1 2 mg/kg rat | Control | HDL 0.2 ml/kg rat | 0.2 ml of HDL + 2 mg of compound 1/ kg rat |
|---|---|---|---|---|---|---|
| 8  | 0 | 0 | 0 | 0 | 0 | 0 |
| 9  | 0 | 0 | 0 | 0 | 0 | 0 |
| 10 | 0 | 0 | 0 | 0.1 ± 0.3 | 0.2 ± 0.5 | 0 |
| 11 | 0 | 0 | 0.5 ± 1.1 | 1.3 ± 0.8 | 1.3 ± 0.9 | 0 |
| 12 | 0 | 0 | 1.4 ± 1.5 | 3.2 ± 0.7 | 2.3 ± 1.1 | 0 |
| 13 | 0 | 0 | 2.7 ± 1.4 | 4.6 ± 0.5 | 3.6 ± 0.8 | 0 |
| 14 | 0 | 0 | 3.8 ± 1.6 | 5.8 ± 0.9 | 4.8 ± 0.4 | 0.2 ± 0.5 |
| 15 | 0 | 0.7 ± 0.8 | 4.5 ± 1.5 | 6.6 ± 0.8 | 5.7 ± 1.0 | 0.4 ± 1.0 |
| 16 | 0.3 ± 0.5 | 2.4 ± 1.0 | 4.5 ± 1.4 | 6.8 ± 0.7 | 6.8 ± 0.5 | 1.5 ± 1.3 |
| 17 | 0.6 ± 0.8 | 3.6 ± 0.7 | 3.2 ± 2.3 | 7.0 ± 0 | 7.0 ± 0 | 2.0 ± 1.4 |
| 18 | 1.2 ± 0.9 | 3.8 ± 0.6 | 2.9 ± 2.4 | | | 2.6 ± 1.9 |
| 19 | 1.8 ± 0.9 | 3.3 ± 0.5 | 2.6 ± 2.5 | | | 2.5 ± 1.6 |
| 20 | 2.2 ± 1.2 | 1.9 ± 0.4 | 2.5 ± 2.5 | | | 1.8 ± 1.4 |
| 21 | 2.3 ± 1.4 | 1.6 ± 0.5 | 2.4 ± 2.6 | | | 1.4 ± 1.2 |
| 22 | 2.3 ± 1.5 | 1.2 ± 0.4 | 2.4 ± 2.7 | | | 1.4 ± 1.2 |
| 23 | 2.0 ± 1.9 | 1.0 ± 0.4 | 2.2 ± 2.8 | | | 0.9 ± 0.7 |

TABLE 1-continued

| | Compound 1 | | | | HDL | 0.2 ml of HDL + 2 mg of |
| --- | --- | --- | --- | --- | --- | --- |
| Days after injection | 20 mg/kg rat | 10 mg/kg rat | 2 mg/kg rat | Control | 0.2 ml/kg rat | compound 1/ kg rat |
| 24 | 1.4 ± 2.1 | 0.8 ± 0.7 | 2.0 ± 2.8 | | | 0.5 ± 0.7 |
| 25 | 1.2 ± 2.1 | 0.2 ± 0.4 | 1.7 ± 2.8 | | | 0.2 ± 0.4 |
| 26 | 0.9 ± 2.3 | 0 | 1.4 ± 3.0 | | | 0 |
| 27 | 0.7 ± 2.2 | | 1.4 ± 3.0 | | | |

The results show that all animals in the control group and 0.2 ml of HDL group die within 17 days. In the treatment groups 10 mg of compound 1 and 20 mg of compound 1, a delayed onset of the disorder takes place and the symptoms disappear after approximately 26 days. In the treatment group 2 mg of compound 1 distinctly more severe symptoms occur and the symptoms subside more slowly. In the treatment group 0.2 ml of HDL and 2 mg of compound 1—preparation according to the invention—a delayed onset of the disorder takes place and the symptoms disappear after 25 days. The delaying of the disorder in the treatment group 0.2 ml of HDL and 2 mg of compound 1 corresponds approximately to the treatment group 10 mg of compound 1 and the severity of the symptoms occurring corresponds approximately to the treatment group 20 mg of compound 1. The preparation according to the invention therefore leads to a reduction in the dose of compound 1 with equally good activity.

EXAMPLE 3

Sodium N-(4-trifluoromethylphenyl)-2-cyano-3-hydroxyhept-2-en-6-yne-carboxamide (Compound 2)

50 g (0.15 mol) of N-(4-trifluoromethylphenyl)-2-cyano-3-hydroxyhept-2-en-6-yne-carboxamide are dissolved in a two-phase system of 50 ml of 5N sodium hydroxide solution and 500 ml of ethyl acetate, and the organic phase is separated off, washed twice with a little water, dried over sodium sulfate and concentrated. The oily residue is taken up with 500 ml of tertiary-butyl methyl ether and, for complete crystallization, stirred at room temperature for 4 hours (h), filtered and dried under reduced pressure. To completely remove solvent residues, the crystalline product is suspended under reflux in 500 ml of toluene for 10 min, cooled with stirring, filtered off with suction again and dried under reduced pressure. Yield: 41.1 g (77%) of melting point $^3$244° C. decomposition (dec.).

$C_{15}H_{10}F_3N_2O_2Na$ (330.24 g/mol): calculated C: 54.0 H: 3.5 N: 8.4 Na: 6.88 (calc. for 1.1% water) found C: 54.4 H: 3.4 N: 8.4 Na: 6.5 water: 1.1%

EXAMPLE 4

Sodium 2-cyano-3-cyclopropyl-3-hydroxy-N-(4-cyanophenyl)acrylamide (Compound 3)

15 g (0.059 mol) of 2-cyano-3-cyclopropyl-3-hydroxy-N-(4-cyanophenyl)-acrylamide are suspended in 120 ml of water and 100 ml of acetone and brought into solution by addition of 60 ml of 1N NaOH. After filtration of traces of undissolved material, the mixture is concentrated to approximately 200 ml under reduced pressure on a rotary evaporator, and the residue is crystallized overnight at 0° C., filtered off with suction and dried under reduced pressure.

Yield: 13 g, m.p. >280° C. $C_{14}H_{10}N_3Na$ (275.24): calculated C: 60.7 H: 3.7 N: 15.2 (calc. for 0.7% water) found C: 60.8 H: 3.6 N: 15.3 water: 0.7%

EXAMPLE 5

Influence of HDL in the Acute Transplantation Rejection Test Model

The experiment is carried out as described in H. U. Schorlemmer et al. (Transplant. Proceeding, Volume 25, No. 1 (1993), pages 763–767). The transplant donors used are female dark Agouti rats (RTI*avl); recipient rats are Lewis rats (RTI*I) having a body weight of approximately 170 g. The rats are available from Charles River-Wega, Sulzfeld, Germany.

Pieces of skin from the tail, size approximately 0.5×1.0 cm, are transferred from the dark Agouti rats (DA) to the tail of the Lewis rats (LEW). 8 animals are employed per treatment group. Rejection is defined as transplanted skin having a hard consistency and reddish-brown color. The compounds 1, 2 and 3 and the HDL fractions are prepared as in Example 2 and administered to the animals intravenously (i.v.). The treatment with the preparations is carried out once per day on the day of transplantation and the nine (9) following days.

Table 2 shows the results.

TABLE 2

| Compounds administered | Day on which rejection of the transplant takes place | Average rejection time (days; x ± SD) |
| --- | --- | --- |
| Control | 7, 7, 7, 8, 8 | 8.3 ± 1.2 |
| 0.4 ml HDL | 9, 9, 9 | |
| Compound 1 2.5 mg/kg rat/day | 18, 18, 18, 19, 20 20, 21, 21 | 19.4 ± 1.3 |
| 0.4 ml HDL + 2.5 mg compound 1/ kg rat/day | 32, 32, 33, 33, 33 33, 33, 34 | 32.9 ± 0.6 |
| Compound 1 5 mg/kg rat/day | 23, 23, 23, 23, 23 24, 26, 26 | 23.8 ± 1.4 |
| 0.4 ml HDL + 5 mg compound 1/ kg rat/day | 34, 34, 35, 35, 36, 36, 37, 37 | 35.5 ± 1.2 |
| Compound 2 2.5 mg/kg rat/day | 12, 13, 13, 13, 14 15, 18, 18 | 14.5 ± 2.3 |
| 0.4 ml HDL + 2.5. mg compound 2/ kg rat/day | 21, 23, 24, 24, 25 25, 25, 26 | 24.1 ± 1.6 |
| Compound 2 5 mg/kg rat/day | 15, 16, 18, 18, 18 19, 19, 21 | 18.0 ± 1.9 |
| 0.4 ml HDL + 5 mg compound 2/ kg rat/day | 25, 25, 27, 27, 29 30, 30, 31 | 28.0 ± 2.3 |
| Compound 3 2.5 mg/kg rat/day | 13, 13, 14, 14, 16 17, 18, 18 | 15.4 ± 2.1 |
| 0.4 mg HDL + | 21, 22, 22, 22, 23 | 22.6 ± 1.1 |

TABLE 2-continued

| Compounds administered | Day on which rejection of the transplant takes place | Average rejection time (days; x ± SD) |
|---|---|---|
| 2.5 mg compound 3/ kg rat/day | 23, 24, 24 | |
| Compound 3 5 mg/kg rat/day | 16, 16, 17, 18, 19 20, 22, 22 | 18.8 ± 2.4 |
| 0.4 ml HDL + 5 mg compound 3/ kg rat/day | 24, 24, 25, 25, 26 27, 29, 29 | 26.1 ± 2.0 |

Table 2 shows that preparations containing HDL and a compound of the formula I distinctly prolong the rejection time.

EXAMPLE 6

Influence of LDL in the Acute Transplanation Rejection Model

LDL is prepared essentially as described in example 1a) from rat serum. The animals are treated as described in example 5. The treatment with the preparations is carried out once per day on the day of transplantation and the fourteen (14) following days.

Table 3 shows the results.

TABLE 3

| Compounds administered | Day on which rejection of the transplant takes place | Average rejection time (days; x ± SD) |
|---|---|---|
| Control | 13, 14, 14, 15, 15, 15, 15, 16, 16, 16 | 14.9 ± 1.0 |
| 0.4 ml LDL | | |
| Compound 1 2.5 mg/kg rat/day | 22, 23, 23, 23, 23 24, 24, 25, 25, 26 | 23.8 ± 1.2 |
| 0.4 ml LDL + 2.5 mg compound 1/ kg rat/day | 35, 36, 36, 37, 37, 37, 37, 38, 38, 38 | 36.9 ± 1.0 |
| Compound 1 5 mg/kg rat/day | 26, 27, 27, 28, 28, 29, 29, 29, 30, 30 | 28.3 ± 1.3 |
| 0.4 ml LDL + 5 mg compound 1/ kg rat/day | 40, 40, 40, 40, 41 41, 41, 41, 42, 42 | 40.8 ± 0.8 |
| Compound 2 2.5 mg/kg rat/day | 18, 18, 19, 19, 19 20, 20, 21, 21, 21 | 19.6 ± 1.2 |
| 0.4 ml LDL + 2.5 mg compound 2/ kg rat/day | 28, 28, 28, 29, 30 31, 31, 31, 31, 32 | 29.9 ± 1.5 |
| Compound 2 5 mg/kg rat/day | 22, 23, 24, 24, 24 24, 24, 25, 25, 25 | 24.1 ± 1.0 |
| 0.4 ml LDL + 5 mg compound 2/ kg rat/day | 35, 35, 36, 36, 36 37, 37 37, 37, 38 | 36.4 ± 1.0 |
| Compound 3 2.5 mg/kg rat/day | 19, 19, 19, 20, 20 21, 21, 21, 21, 22 | 20.3 ± 1.1 |
| 0.4 mg LDL + 2.5 mg compound 3/ kg rat/day | 28, 28, 29, 29, 29 30, 30, 31, 31, 32 | 29.7 ± 1.3 |
| Compound 3 5 mg/kg rat/day | 23, 23, 23, 24, 24 24, 24, 24, 25 25 | 23.9 ± 0.7 |
| 0.4 ml LDL + 5 mg compound 3/ k rat/day | 34, 34, 34, 35, 35 35, 36, 36, 36, 37 | 35.2 ± 1.0 |

Table 3 shows that preparations containing LDL and a compound of the formula I distinctly prolong the rejection time.

We claim:
1. A composition comprising
   1) a lipoprotein, and
   2) a compound of the formula I

$$NC-\underset{\underset{HO}{\overset{\parallel}{C}}}{\overset{O}{\overset{\parallel}{C}}}-\overset{O}{\overset{\parallel}{C}}-NH-\underset{R_1}{\overset{}{\diagup}}\diagdown\underset{X}{=}\underset{R^3}{\overset{R^2}{\diagup}}$$ (I)

or a sterioisomeric form of the compound of formula I, or a salt thereof, wherein
   $R^1$ is
      a) $(C_1-C_4)$-alkyl,
      b) $(C_3-C_5)$-cycloalkyl,
      c) $(C_2-C_6)$-alkenyl or
      d) $(C_2-C_6)$-alkynyl,
   $R^2$ is
      a) $-CF_3$,
      b) $-O-CF_3$,
      c) $-S-CF_3$,
      d) $-OH$,
      e) $-NO_2$,
      f) halogen,
      g) benzyl,
      h) phenyl,
      i) $-O$-phenyl,
      k) $-CN$ or
      l) $-O$-phenyl, mono- or polysubstituted by
         1) $(C_1-C_4)$-alkyl,
         2) halogen,
         3) $-O-CF_3$ or
         4) $-O-CH_3$,
   $R^3$ is
      a) $(C_1-C_4)$-alkyl,
      b) halogen, or
      c) a hydrogen atom, and
   X is
      a) a $-CH$ group or
      b) a nitrogen atom.
2. The composition of claim 1, wherein
   $R^1$ is
      a) methyl,
      b) cyclopropyl or
      c) $(C_3-C_5)$-alkynyl,
   $R^2$ is $CF_3$ or $CN$,
   $R^3$ is a hydrogen atom or methyl, and
   X is a $-CH$ group.
3. The composition of claim 1, wherein the compound of formula I is N-(4-trifluoromethylphenyl)-2-cyano-3-hydroxycrotonamide, 2-cyano-3-cyclopropyl-3-hydroxy-N-(4-cyanophenyl)acrylamide or N-(4-trifluoromethylphenyl)-2-cyano-3-hydroxyhept-2-en-6-yne-carboxamide, or a stereoisomeric form of the compound of formula I or a salt thereof.
4. The composition of claim 1, wherein the lipoprotein is a high density lipoprotein fraction, high density lipoprotein subfraction or a high density lipoprotein constituent is employed.
5. The composition of claim 4, wherein the high density lipoprotein or apolipoprotein employed is $HDL_1$, $HDL_2$, HDL3, $HDL_c$, Apo E, Apo A-I, Apo A-II, modified forms thereof, or a mixture thereof.
6. The composition of claim 1, which further comprises one or more antiuricopathic agent, platelet aggregation inhibitor, analgesic, steroidal antiinflammatory agent, non-steroidal antiinflammatory agent or immunosuppressive compound.

7. The composition of claim 6, which further comprises cyclosporin A, FK 506 or rapamycin.

8. A process for the production of the composition of claim 1, comprising admixing a lipoprotein and a compound of the formula I, a stereoisomeric form or salt thereof.

9. The process of claim 8, further comprising admixing a lipoprotein, a compound of formula I, a stereoisomer form or salt thereof, and a pharmaceutical excipient to give a pharmaceutical administration form.

10. A method for the treatment of an acute, chronic or hyperacute rejection reaction after organ transplantation which comprises administering to a host in need of such treatment, an effective amount of a composition as claimed in claim 1.

11. A method for the treatment of an immunological disorder or an autoimmune disease which comprises administering to a host in need of such treatment, an effective amount of a composition as claimed in claim 1.

12. A method for the treatment of type II diabetes which comprises administering to a host in need of such treatment, an effective amount of a composition as claimed in claim 1.

13. A method for the treatment of a carcinomatous disorder which comprises administering to a host in need of such treatment, an effective amount of a composition as claimed in claim 1.

14. The method according to claim 13, wherein the carcinomatous disorder is lung cancer, leukemia, ovarian cancer, sarcoma, Kaposi's sarcoma, meningioma, colonic cancer, lymph node cancer, brain tumors, breast cancer, pancreatic cancer, prostatic cancer or skin cancer.

15. A pharmaceutical composition comprising an effective amount of a composition as claimed in claim 1 together with a pharmaceutically acceptable carrier.

16. A method for the treatment of an acute, chronic or hyperacute rejection reaction after organ transplantation which comprises administering to a host in need of such treatment, a pharmaceutical composition as claimed in clam 15.

17. A method for the treatment of an immunological disorder which comprises administering to a host in need of such treatment, a pharmaceutical composition as claimed in claim 15.

18. A method for the treatment of an autoimmune disease which comprises administering to a host in need of such treatment, a pharmaceutical composition as claimed in claim 15.

19. A method for the treatment of type II diabetes which comprises administering to a host in need of such treatment, a pharmaceutical composition as claimed in claim 15.

20. A method for the treatment of a carcinomatous disorder which comprises administering to a host in need of such treatment, a pharmaceutical composition as claimed in claim 15.

21. The method according to claim 20, wherein the carcinomatous disorder is lung cancer, leukemia, ovarian cancer, sarcoma, Kaposi's sarcoma, meningioma, colonic cancer, lymph node cancer, brain tumors, breast cancer, pancreatic cancer, prostatic cancer or skin cancer.

* * * * *

UNITED STATES PATENT AND TRADEMARK OFFICE
CERTIFICATE OF CORRECTION

PATENT NO. : 5,780,592
DATED : July 14, 1998
INVENTOR(S) : Müllner et al.

It is certified that error appears in the above-identified patent and that said Letters Patent is hereby corrected as shown below:

Title Page, Item [57], in the Abstract, in Formula I,

" 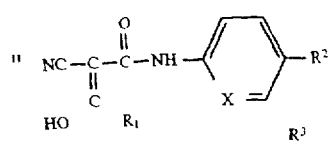 " should read -- 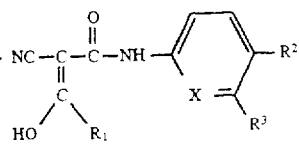 --

Claim 5, column 12, line 61, "HDL3" should read --$HDL_3$--.

Signed and Sealed this

Sixth Day of March, 2001

Attest:

NICHOLAS P. GODICI

Attesting Officer    Acting Director of the United States Patent and Trademark Office